US 6,701,000 B1

(12) United States Patent
Hsieh

(10) Patent No.: US 6,701,000 B1
(45) Date of Patent: Mar. 2, 2004

(54) SOLUTION TO DETECTOR LAG PROBLEM IN A SOLID STATE DETECTOR

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/302,603

(22) Filed: Apr. 30, 1999

(51) Int. Cl.$^7$ .................................................. G06K 9/00
(52) U.S. Cl. .............................. 382/131; 378/4; 378/8; 378/12; 378/62
(58) Field of Search ............................ 382/131, 132, 382/128, 129, 130; 378/4, 8, 57, 62, 12; 600/410, 413, 437, 559; 250/300, 303.09, 332, 548

(56) References Cited

U.S. PATENT DOCUMENTS

| 4,550,371 A | * | 10/1985 | Glover et al. | .................. 378/4 |
| 4,580,219 A | * | 4/1986 | Pelc et al. | .................. 382/131 |
| 4,752,879 A | * | 6/1988 | Brunnett | .................. 378/19 |
| 4,858,128 A | * | 8/1989 | Nowak | .................. 382/131 |
| 4,914,589 A | * | 4/1990 | Crawford | .................. 382/131 |
| 5,361,291 A | * | 11/1994 | Toth et al. | .................. 378/12 |
| 5,552,605 A | * | 9/1996 | Arata | .................. 250/363.04 |
| 5,845,003 A | * | 12/1998 | Hu et al. | .................. 382/131 |
| 5,969,360 A | * | 10/1999 | Lee | .................. 378/19 |
| 6,115,445 A | * | 9/2000 | Lai | .................. 378/4 |
| 6,256,404 B1 | * | 7/2001 | Gordon et al. | .................. 382/131 |

* cited by examiner

Primary Examiner—Jayanti K. Patel
Assistant Examiner—Abolfazl Tabatabai
(74) Attorney, Agent, or Firm—Carl B. Horton, Esq.; Armstrong Teasdale LLP

(57) ABSTRACT

The present invention, in one form, includes a digital x-ray imaging system which, in one embodiment, collects projection data from a plurality of views and reduces artifacts caused by detector residual signals. More specifically and in one embodiment, volumetric images are generated by collecting projection data for a plurality of views. During inactive periods between the collection of projection data for adjacent views, the x-ray emission is stopped and each detector pixel is simultaneously energized to reduce a residual signal of each pixel. As a result, projection data for a subsequent view is not biased by the residual signal from a previous view.

23 Claims, 2 Drawing Sheets

SOLUTION TO DETECTOR LAG PROBLEM IN A SOLID STATE DETECTOR

BACKGROUND OF THE INVENTION

This invention relates generally to an imaging system, and more particularly, to reducing artifacts caused by detector signal lag.

In at least one known imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location.

In at least one known type of imaging system, commonly known as a computed tomography (CT) system, a group of x-ray attenuation measurements, i.e., projection data, from the detector array is referred to as a "view". A "scan" of the object comprises a set of views made at different projection angles, or view angles, during at least one revolution of the x-ray source and detector. In an axial scan, the projection data is processed to construct an image that corresponds to a two dimensional slice taken through the object. Typically, each slice represents less than approximately 2 cm of coverage of the patient in the patient or z-axis and is generated from data collected from 984 views during a rotation of the gantry. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT system collects data utilizing a large flat panel digital x-ray device, or detector, having a plurality of pixels arranged in rows and columns. However, such flat panels suffer from detector lag. The detector lag causes a significant portion of the signals from previous samples to incorrectly bias subsequent samples. A significant cause of the lag is related to the electron de-trapping resulting from the high density electronic defects in an energy gap. De-trapping times range from a few milliseconds to as long as 100 seconds. As a result of the non-uniformity of the lag, artifacts, such as rings and bands, occur in the reconstructed images.

It is desirable to provide an imaging system which utilizes a solid-state detector to generate substantially "artifact free" volumetric images. It would also be desirable to provide such a system which reduces a detector lag artifacts without significantly increasing the time required to generate the images.

BRIEF SUMMARY OF THE INVENTION

These and other objects may be attained in a digital x-ray imaging system which, in one embodiment, collects projection data from a plurality of views and reduces detector residual signals between the collection of adjacent views. More specifically and in one embodiment, the imaging system includes an x-ray source and at least one solid-state x-ray detector. To generate volumetric images, at least one of the x-ray source and the x-ray detector are rotated around the object of interest. For each identified view, x-rays are emitted from the x-ray source toward the x-ray detector and projection data is collected for the view. During an inactive period between the collection of projection data for adjacent views, the emission of x-rays is stopped and each pixel of the detector is simultaneously energized at least once.

More specifically, during the inactive period, each scan line of the detector is simultaneously energized. The simultaneous energizing of all of the scan lines reduces a residual signal of each pixel. As a result, when projection data is collected for a subsequent view, the signal level of each pixel more accurately reflects the attenuation of the object of interest for the current view. Using the projection data collected for the plurality of views, cross-sectional images of the object of interest are generated.

Using the above described imaging system, detector lag artifacts are reduced to generate substantially "artifact free" volumetric images. In addition, the system does not significantly increase the amount of time required to generate the images.

DETAILED DESCRIPTION OF THE INVENTION

Figure 1:
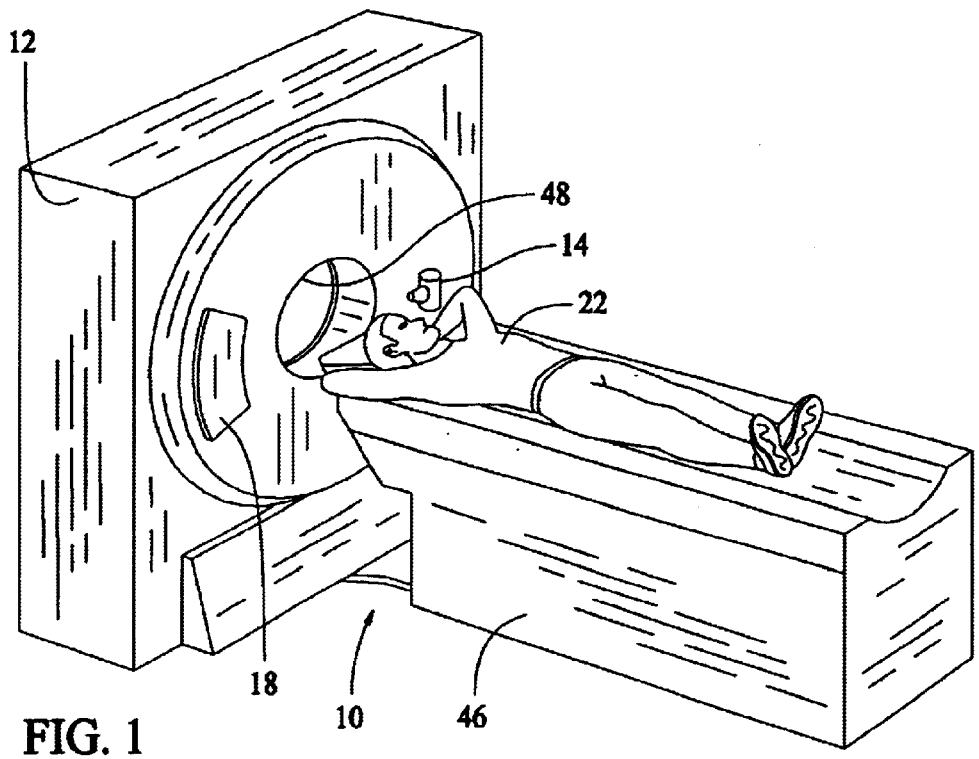
FIG. 1 is a pictorial view of a digital imaging system.
Figure 2:
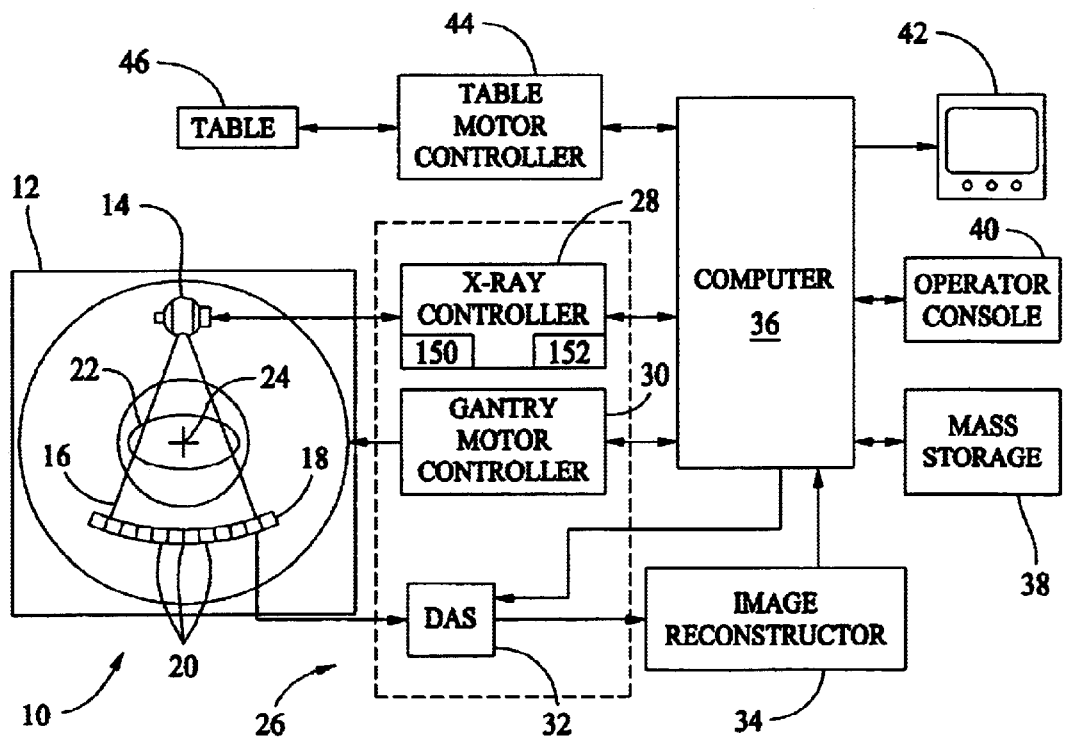
FIG. 2 is a block schematic diagram of the system illustrated in FIG.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam is collimated by a collimator (not shown) to lie within in an X-Y plane of a Cartesian coordinate system and generally referred to as an "imaging plane". Detector array 18 is formed by a plurality of pixels, or elements (not shown in FIG. 1) which together sense the projected x-rays that pass through a medical patient 22. Each detector element produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
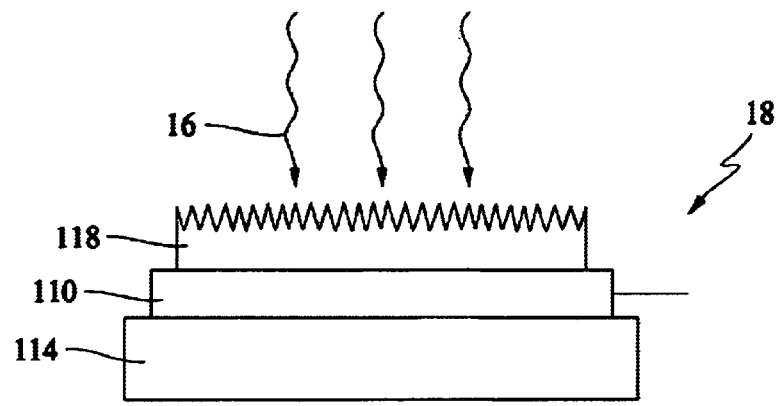
FIG. 3 is a schematic diagram of an x-ray detector illustrated in FIG. 1.
Figure 4:
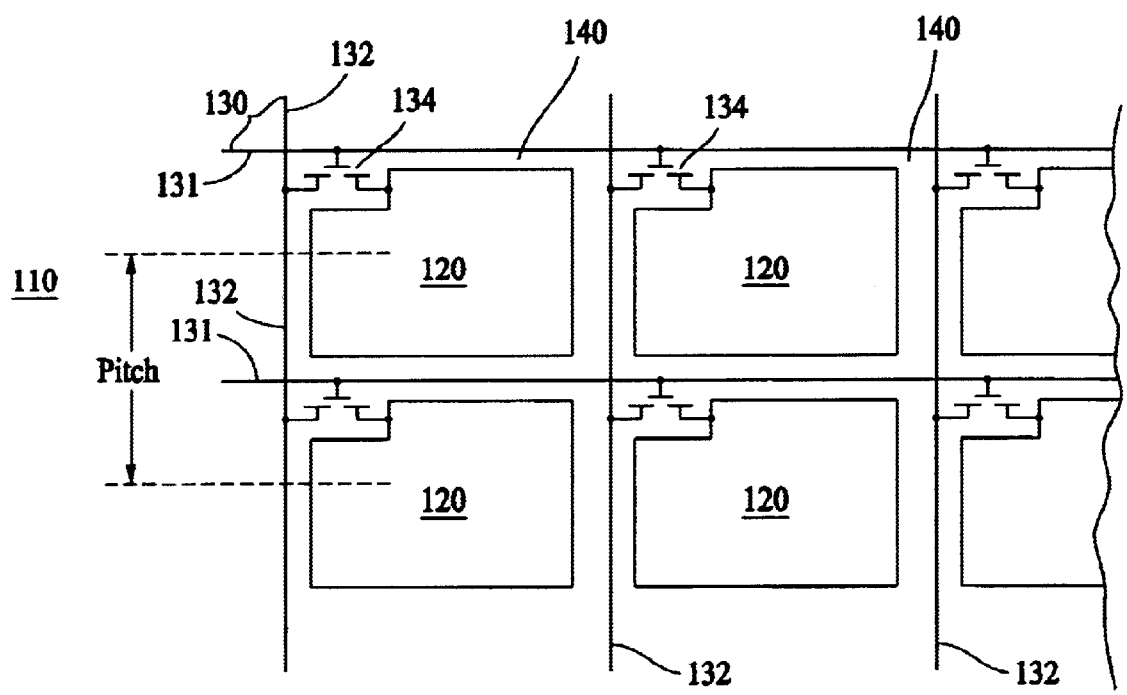
FIG. 4 is a schematic diagram of an x-ray detector illustrated in FIGS. 1 and 3.

In one embodiment and as shown in FIGS. 3 and 4, detector 18 is a solid-state detector or radiation imager in a large flat panel configuration having a photosensor array 110 disposed on a substrate 114 and a scintillator 118 disposed on photosensor array 110. Scintillator 118 is disposed so as to receive and absorb incident radiation, e.g., x-ray beam 16. Scintillator 118 is optically coupled to photosensor array 110 so that optical photons generated in scintillator 118 pass into photosensor array 110. Photosensor array 110 includes a plurality of photosensors 120, such as photodiodes, and an addressable thin film transistor (TFT) array 130 electrically coupled to each photosensor 120. In one embodiment, each photosensor 120 includes an amorphous silicon (a-Si) photodiode (not shown).

Addressable TFT array 130 comprises address lines 131, 132, typically known respectively as scan lines 131 and data lines 132, and a plurality of charge retention TFTs 134. Scan lines 131 and data lines 132 are arranged in rows and columns so as to divide photosensor array 110 into a plurality of pixels 140, with one photosensor 120 disposed in each pixel 140 and electrically coupled to a respective charge retention TFT 134, which is in turn electrically coupled to one scan line 131 and one data line 132. Addressable TFT array 130 is configured so that each photosensor 120 is selectively and respectively addressable, that is each photosensor output (not shown) is selectively electrically coupled to its corresponding data line 132. The radiation incident on scintillator 118 and pixel photosensors 120 measure, by way of change in the charge across the photodiode, the amount of light generated by x-ray interaction with scintillator 118. As a result, each pixel 140 produces a digital electrical output signal that represents the intensity, after attenuation of patient 22, of an impinging x-ray beam 16. In this manner each photosensor 120 generates projection data. More specifically, the output signal of each respective photosensor 120 is respectively coupled to DAS 32 so that charge accumulated in each photodiode is transmitted to an input channel (not shown) of DAS 32. In one embodiment, detector 18 is 40 cm by 40 cm and is configured to produce projection data for an entire object of interest. More specifically, each pixel 140 is approximately 200 uM by 200 uM and detector 18 includes an array of 2,000 pixels×2,000 pixels.

In operation, at least one image of patient 22 is generated by collecting projection data from a plurality of projection, or view angles. In one embodiment, each image is generated by rotating at least one of x-ray source 14 and x-ray detector 18 around patient 22 and collecting projection data from detector 18. More specifically and in one embodiment, a volumetric image of at least a portion of patient 22 is generated by collecting projection data from a plurality of views. Utilizing the speed limitation of detector array 18 and a scan time of 5 seconds, system 10, in one embodiment, collects projection data from 300 views spaced approximately 1.2 degrees apart (360 degrees/300 views).

After identifying the number and location, or spacing, of the views, the projection data is collected for each view utilizing detector 18. Specifically and in one embodiment, as at least one of x-ray source 14 and detector 18 is rotated around patient 22, projection data is collected for each identified view. More specifically, for each identified view, control mechanism transmits an energizing signal to source 14 so that x-rays 16 are emitted from source 14 toward detector 18. The radiation of detector 18, specifically each pixel 140, generates projection data for each identified view. The projection data for the identified view is then transmitted to DAS 32. More specifically, the charge of each charge retention TFT 134 is transmitted to DAS 32. Particularly and in one embodiment, the projection data is measured, or sampled, by sequentially enabling rows of pixels 140 by transmitting an activation signal to a corresponding scan line 131 of detector 18. Upon receiving the activation signal, the output charge signal of each charge retention TFT 134 of the corresponding row of array, are transmitted via corresponding data lines 132 to input channels of DAS 32 and then to image reconstructor 34. More specifically, the activation signal energizes each pixel 140 electrically connected to the energized scan line 131. As a result, each output signal of each pixel 140 electrically connected to the energized scan line 131 is transmitted to DAS 32 via data lines 132. This procedure is then repeated for each row of array 110 for the identified view, by sequentially energizing each scan line 131 and measuring, or sampling, the output signal of each pixel 140 of the corresponding row of array 110.

For example, where detector 18 includes an array of M×N pixels, where M is a number of columns and N is a number of rows, projection data for a first view angle is collected by emitting x-rays 16, at a first view angle, toward detector 18. Output signals of pixel 140 are then measured using DAS 32. Specifically, after energizing activation signal of row 1 via row 1 scan line 131, the output signal of each of M data lines 132 is transmitted to DAS 32 and then to image reconstructor 34. The activation signal of row 1 is then de-energized and the activation signal of row 2 is energized. The output signal of each data line 132 is then transmitted to DAS 32 and then to image reconstructor 34. This process is repeated until the activation signal of the Nth row has been energized and the output signal of data lines 132 transmitted to DAS 32. In one embodiment, where detector 18 includes 2000 rows and the sampling rate is 60 frames per second, a read-out rate for each row is 0.0083 milliseconds.

After collecting projection data for the identified view and at least one of source 14 and detector 18 continues to rotate about patient 22, control mechanism 26 alters the signals transmitted to source 14 so that x-rays 16 are no longer emitted from source 14. More specifically, in order to minimize blurring caused by the large angular span between views, the emission of x-rays 16 is limited to a determined period of time. For example, where it is determined that the resolution requirements require a "smearing" in a view to be less than 0.6 degrees, source 14 will emit x-rays 16 for 50% of the time between projections.

For example, if it is determined that x-ray source 14 must be enabled for approximately 0.5 degrees for each view to satisfy the resolution requirement of system 10, x-ray source 14 is enabled for 0.5 degrees. During the time that source 14 is enabled, projection data is collected from detector 18. Thereafter, x-ray source 14 is disabled. More specifically, the voltage and current signals are removed, or altered, so that x-ray beam 16 is no longer emitted from source 14.

In one embodiment, x-ray controller 28 includes a power supply 150 and a switching unit, or circuit 152, as known in the art, to alter the signals supplied to source 14. Power supply 150 is coupled to x-ray tube 14 and switching unit 152 to supply signals to source 14 and unit 152. More particularly, voltage and current signals from supply 150 are supplied to an anode (not shown) and a cathode (not shown) of source 14. A high voltage signal is also supplied from supply 150 to switching unit 152. If x-ray beams 16 are to be emitted, the proper voltage and current signals are transmitted to x-ray source 14. More specifically, utilizing control signals (not shown) supplied to switching unit 152, for example, signals from computer 36, switching unit 152 alters the signals supplied to source 14. More specifically, by altering the control signals, the signal supplied to a control grid (not shown) of source 14 is altered so that the speed at which the electrons travel from the anode to the cathode is modified, therefore, altering the magnitude and duration of x-ray beams 16 emitted from source 14. As a result, the emission of x-rays 16 may be started or stopped at specific, or defined, periods of time.

During the period of time that x-rays 16 are not emitted from source 14 between adjacent views, referred to as an inactive period of time, each pixel 140 maintains a portion of the output signal generated for the view last collected. This signal is defined as a residual signal of detector 18. The residual signal results from "detrapping" of interband states in the semiconductive material (not shown) of a switching device of each pixel 140, such as a FET (not shown) after the FET is turned off, e.g.,the time period when a signal is not desired from pixel 140.

System 10 reduces the artifacts caused by the residual signal by reducing the level of the residual signals during the time between adjacent views when x-ray source 14 is disabled (e.g., during the inactive period). Specifically and in one embodiment, during the inactive period, the residual signal of each pixel 140 is reduced by energizing, or enabling, a plurality of rows of each detector 18 at least once. More specifically and in one embodiment, activation signals are simultaneously transmitted, at least once, to each pixel 140 via each scan line 131. Depending upon the amount of time available during the inactive period, the simultaneous transmission of the activation signals each scan line 131 is repeated a plurality of times. Each time scan lines 131 are simultaneously transmitted to detector 18, the residual charge of each pixel 140 is reduced. In one embodiment, the residual charge of charge retention TFT 134 is reduced as a function of 1/S, where S is a number of samples. As a result of the simultaneous transmission of the activation signals, the residual signal of each pixel 140 of detector 18 may be rapidly reduced.

For example, where detector 18 includes a 2,000 column by 2,000 row array of pixels 140 and activation signals are simultaneously applied to all 2,000 scan lines 131 twenty times, once every 0.0083 milliseconds, during the inactive period, the residual signal of each charge retention TFT 134 is reduced to approximately 5% of its original strength.

In one embodiment, the accuracy of the projection data collected for each view is corrected utilizing a lag correction value. More specifically, based upon the number of times each scan line 131 is simultaneously enabled, a lag correction value may be determined and combined with the collected projection data to further reduce the image artifacts caused by the residual signals. In various embodiments, the lag correction value is based on actual historical data, estimated values, or mathematical calculations for each detector 18.

At the end of the inactive period, the above described process is repeated for each view until projection data has been collected for each identified view. The collected projection data is then utilized, in a manner known the art, to generate at least one image of an object of interest, for example a portion of patient 22. More specifically, and in one embodiment, cross-sectional images of the object of interest are generated from the projection data. In another embodiment, the corrected projection data is utilized to generate the images of the object of interest.

The above described system reduces artifacts caused by charge retention of a solid-state detector array. Particularly, by simultaneously energizing each scan line of the detector array, the residual signal of the detector is reduced.

While the invention has been described in terms of various specific embodiments, those skilled in the art will recognize that the invention can be practiced with modification within the spirit and scope of the claims. For example, although the present invention was described in use with a CT system, the invention may be practiced with many other types of imaging systems.

What is claimed is:

1. A method for reducing image artifacts in an imaging system, the imaging system including an x-ray source for emitting an x-ray beam and at least one solid state x-ray detector, said method comprising the steps of:
   collecting projection data for a plurality of views; and
   reducing residual signal levels of each detector between adjacent views wherein reducing the residual signal levels comprises:
   disabling the x-ray source between collection of projection data for adjacent views; and
   applying at least one activation signal to each dector.

2. A method in accordance with claim 1 wherein collecting projection data for a plurality of views comprises the steps of:
   identifying each view; and
   enabling the x-ray source and collecting projection data for each identified view using each detector.

3. A method in accordance with claim 2 wherein enabling the x-ray source and collecting projection data for each identified view using each detector comprises the steps of:
   determine whether x-ray beams are to be emitted from the x-ray source; and
   if the x-ray beams are to be emitted, provide a voltage and current signal to the x-ray source.

4. A method in accordance with claim 1 wherein each detector includes a plurality of pixels arranged in an array of M rows and N columns, and wherein applying at least one activation signal to each detector comprises the step of applying an activation signal to each pixel of each detector.

5. A method in accordance with claim 4 wherein each digital detector includes M output signals and N activation signals, and wherein applying an activation signal to each pixel of each detector comprises the step of a) enabling all N activation signals of each detector simultaneously.

6. A method in accordance with claim 5 further comprising the step of repeating step a) at least once.

7. A method in accordance with claim 5 further comprising the step of repeating step a) a plurality of times.

8. A method in accordance with claim 5 wherein M equals 2000 and N equals 2000.

9. A method in accordance with claim 1 further comprising the step of correcting the projection data utilizing a lag correction value for each detector.

10. A method in accordance with claim 9 further comprising the step of generating cross-sectional images of an object of interest using the corrected projection data.

11. An imaging system for reducing image artifacts, said imaging system comprising an x-ray source for emitting an x-ray beam and at least one solid state x-ray detector, said system configured to:

collect projection data for a plurality of views; and reduce residual signal levels of each said detector between adjacent views.

12. A system in accordance with claim 11 wherein to collect projection data for a plurality of views, said system configured to:

identifying each view; and enable said x-ray source and collect projection data for each identified view using each said detector.

13. A system in accordance with claim 12 wherein to enable said x-ray source and collect projection data for each identified view using each said detector, said system configured to:

determine whether said x-ray beams are to be emitted from said x-ray source; and if said x-ray beams are to be emitted, provide a voltage and current signal to said x-ray source.

14. A system in accordance with claim 12 wherein each said detector includes a plurality of pixels arranged in an array of M rows and N columns, and wherein to apply at least one activation signal to each said detector, said system configured to apply an activation signal to each said pixel of each said detector.

15. A system in accordance with claim 14 wherein each said detector includes M output signals and N activation signals, and wherein to apply an activation signal to each said pixel of each said detector, said system configured to enable all N said activation signals of each said detector simultaneously.

16. A system in accordance with claim 15 further configured to enable all N said activation signals of each said detector simultaneously at least once.

17. A system in accordance with claim 15 further configured to enable all N said activation signals of each said detector simultaneously a plurality of times.

18. A system in accordance with claim 15 wherein M equals 2000 and N equals 2000.

19. A system in accordance with claim 11 further configured to correct said projection data utilizing a lag correction value for each said detector.

20. A system in accordance with claim 19 further configured to generate cross-sectional images of an object of interest using said corrected projection data.

21. A method of reducing a lag signal in a detector array, the detector array includes a plurality of pixels arranged in columns and rows, each column of pixels electrically connected to a pixel output signal, each row of pixels electrically connected to a pixel activation signal, said method comprising the steps of:

a) enabling a pixel activation signal for a row of the detector array;

b) measuring a pixel output signal for each pixel corresponding to the enabled row; and c) repeating steps a) and b) for each row of the array; and d) simultaneously enabling each pixel activation signal of the detector array at least once.

22. A method in accordance with claim 21 wherein the detector array includes M columns and N rows, and wherein simultaneously enabling each pixel activation signal of the detector array at least once comprises the step of simultaneously enabling N pixel activation signals at least once.

23. A method in accordance with claim 22 wherein simultaneously enabling each pixel activation signal of the detector array at least once comprises the step of simultaneously enabling N pixel activation signals a plurality of times.

* * * * *

UNITED STATES PATENT AND TRADEMARK OFFICE
CERTIFICATE OF CORRECTION

PATENT NO. : 6,701,000 B1
DATED : March 2, 2004
INVENTOR(S) : Hsieh

Page 1 of 1

It is certified that error appears in the above-identified patent and that said Letters Patent is hereby corrected as shown below:

Column 6,
Line 5, after "each detector between adjacent views" and insert therefor -- , --.
Line 9, after "one activation signal to each" delete "dector" and insert therefor
-- detector --.

Column 7,
Line 4, after "each said detector between adjacent views" delete "." and insert therefor
-- , wherein to reduce residual signal levels, said imaging system further configured to:
    disable said x-ray source between collection of projection data for adjacent views;
and apply at least one activation signal to each said detector. --.

Signed and Sealed this

Thirteenth Day of December, 2005

JON W. DUDAS
*Director of the United States Patent and Trademark Office*